(12) United States Patent
Liu et al.

(10) Patent No.: US 12,162,831 B2
(45) Date of Patent: Dec. 10, 2024

(54) METHOD FOR PRODUCING METHYL ACETATE BY MEANS OF CARBONYLATION OF DIMETHYL ETHER

(71) Applicant: DALIAN INSTITUTE OF CHEMICAL PHYSICS, CHINESE ACADEMY OF SCIENCES, Liaoning (CN)

(72) Inventors: Hongchao Liu, Liaoning (CN); Wenliang Zhu, Liaoning (CN); Zhongmin Liu, Liaoning (CN); Shiping Liu, Liaoning (CN); Xiangang Ma, Liaoning (CN); Yong Liu, Liaoning (CN); Youming Ni, Liaoning (CN)

(73) Assignee: DALIAN INSTITUTE OF CHEMICAL PHYSICS, CHINESE ACADEMY OF SCIENCES, Liaoning (CN)

( * ) Notice: Subject to any disclaimer, the term of this patent is extended or adjusted under 35 U.S.C. 154(b) by 664 days.

(21) Appl. No.: 17/427,199

(22) PCT Filed: Feb. 2, 2019

(86) PCT No.: PCT/CN2019/074589
§ 371 (c)(1),
(2) Date: Jul. 30, 2021

(87) PCT Pub. No.: WO2020/155143
PCT Pub. Date: Aug. 6, 2020

(65) Prior Publication Data
US 2022/0144748 A1    May 12, 2022

(51) Int. Cl.
  *C07C 67/37*    (2006.01)
  *B01J 21/04*    (2006.01)
  *B01J 29/18*    (2006.01)

(52) U.S. Cl.
  CPC ............... *C07C 67/37* (2013.01); *B01J 21/04* (2013.01); *B01J 29/18* (2013.01)

(58) Field of Classification Search
  CPC ............ C07C 67/37; B01J 21/04; B01J 29/18
  See application file for complete search history.

(56) References Cited

U.S. PATENT DOCUMENTS

2018/0201568 A1 * 7/2018 Liu .................. C07C 69/24
2018/0370896 A1 * 12/2018 Liu ................. B01J 29/7019

FOREIGN PATENT DOCUMENTS

| CN | 101613274 A | 12/2009 | |
| CN | 106365994 A | 2/2017 | |
| CN | 106365995 A | 2/2017 | |
| CN | 106890668 A | 6/2017 | |
| CN | 106890669 A | 6/2017 | |
| CN | 106890671 A | 6/2017 | |
| KR | 10-1391571 B1 | 5/2014 | |
| WO | WO-2017102284 A1 * | 6/2017 | ............. B01J 29/18 |

OTHER PUBLICATIONS

First Office Action dated Nov. 27, 2020 corresponding to Chinese application No. 201910107074.8.
International Search Report dated Oct. 12, 2019 corresponding to application No. PCT/CN2019/074589.

* cited by examiner

*Primary Examiner* — Yate' K Cutliff
(74) *Attorney, Agent, or Firm* — Nath, Goldberg & Meyer; Joshua B. Goldberg

(57) ABSTRACT

Disclosed by the present application is a method for producing methyl acetate by means of the carbonylation of dimethyl ether. The method comprises: passing dimethyl ether and a feed gas comprising carbon monoxide through a reactor loaded with a solid acid catalyst for reaction so as to produce methyl acetate, the molar ratio of carbon monoxide to dimethyl ether being 0.05:1-0.5:1. The described method has the advantages of a low molar ratio of carbon monoxide to dimethyl ether, a high conversion rate of carbon monoxide, a small gas circulation amount, low operation costs and so on.

16 Claims, No Drawings

METHOD FOR PRODUCING METHYL ACETATE BY MEANS OF CARBONYLATION OF DIMETHYL ETHER

FIELD

The present application relates to a method for producing methyl acetate by carbonylation of dimethyl ether, which belongs to the field of catalysis.

BACKGROUND

With the rapid development of modern industry, the contradiction between energy supply and demand has become increasingly prominent. As a major energy-consuming country and also a major energy shortage country, it urgently needs to find alternative energy sources. As a clean energy, ethanol has good miscibility. It can be blended into gasoline as a blending component to partially replace gasoline, increase the octane number and oxygen content of gasoline, effectively promote the full combustion of gasoline, and reduce carbon monoxide and hydrocarbon emissions in automobile exhaust. Ethanol, as a partial substitute for vehicle fuel, can make our country's vehicle fuel present a diversified structural feature. At present, our country mainly uses grain, especially corn, to develop fuel ethanol. Thus, our country has become the third largest fuel ethanol producer and consumer after Brazil and the United States. However, according to our country's national conditions, there are many disadvantages in ethanol production using grain as raw material. The future more development of our country's fuel ethanol will be non-food routes.

Starting from coal resources, the production of ethanol from syngas is an important direction for the development of our country's new coal chemical industry and has broad market prospects. This has important strategic significance and far-reaching impact on the clean utilization of coal resources, alleviating the contradiction of the shortage of oil resources and improving our country's energy security. At present, the process route of coal-to-ethanol is mainly divided into two types: (1) one is the direct production of ethanol from syngas; however, in such process route, a noble metal rhodium catalyst is required, the catalyst cost is high and the output of rhodium is limited; (2) the other is syngas to ethanol via the hydrogenation of acetic acid, in which the syngas is first subjected to liquid phase carbonylation of methanol to produce acetic acid, and then hydrogenated to synthesize ethanol; the latter route is mature, but it requires equipment with special alloys that resist corrosion, and the cost is relatively high; (3) Dimethyl ether is carbonylated with syngas to produce ethanol. In particular, dimethyl ether is firstly carbonylated with syngas to produce methyl acetate, which is then hydrogenated to produce ethanol. The route (3) refers to carbonylation of dimethyl ether and the hydrogenation reaction of methyl acetate. These two reactions use a solid acidic molecular sieve catalyst and a copper-based catalyst respectively, both of which are non-noble metal catalysts, cheap and easy to obtain. Further, the reaction conditions used in these two reactions are mild, and there are no the problem of acetic acid corrosion during the carbonylation and hydrogenation processes, thereby greatly reducing the process cost and equipment cost and achieving the product with high selectivity. Such route is a new coal-to-ethanol route and has a good market prospect.

The carbonylation of dimethyl ether is the core reaction of the syngas to ethanol via the dimethyl ether. In the research of carbonylation of dimethyl ether, the ratio of carbon monoxide to dimethyl ether is relatively high. US20070238897A1 discloses a catalyst for carbonylation of ethers and its use in the carbonylation of dimethyl ether, wherein, during use, the ratio of carbon monoxide to dimethyl ether is 46.5:1 and the catalyst is rapidly deactivated. CN101613274A discloses a mordenite molecular sieve modified by pyridine-based organic amine and its use in carbonylation of dimethyl ether, wherein, during use, the ratio of carbon monoxide to dimethyl ether is 10:1, the conversion rate of dimethyl ether is 30% and the conversion rate of carbon monoxide is about 3%. In the process of industrial application, the ratio of carbon monoxide to dimethyl ether is too high, and thus a large amount of carbon monoxide cannot be converted and utilized. The excess carbon monoxide needs to be recycled after gas separation. The separation, compression, and circulation of gas will inevitably lead to high energy consumption and high operation costs.

SUMMARY

According to one aspect of the present application, a method for producing methyl acetate by carbonylation of dimethyl ether is provided. The method has the advantages of low molar ratio of carbon monoxide to dimethyl ether, high conversion rate of carbon monoxide, small gas circulation amount, and low operation costs.

The method for producing methyl acetate by carbonylation of dimethyl ether is characterized by comprising feeding dimethyl ether and a feeding gas containing carbon monoxide into a reactor loaded with a solid acid catalyst to react to produce methyl acetate; wherein, the molar ratio of carbon monoxide to dimethyl ether ranges from 0.05:1 to 0.5:1.

Optionally, the upper limit of the molar ratio of carbon monoxide to dimethyl ether is 0.06:1, 0.08:1, 0.1:1, 0.12:1, 0.15:1, 0.18:1, 0.2:1, 0.25:1, 0.3:1, 0.35:1, 0.4:1, 0.45:1, 0.48:1, 0.498:1 or 0.5:1; and the lower limit thereof is 0.05:1, 0.06:1, 0.08:1, 0.1:1, 0.12:1, 0.15:1, 0.18:1, 0.2:1, 0.25:1, 0.3:1, 0.35:1, 0.4:1, 0.45:1, 0.48:1 or 0.498:1.

Optionally, the molar ratio of carbon monoxide to dimethyl ether ranges from 0.08:1 to 0.5:1.

Optionally, the molar ratio of carbon monoxide to dimethyl ether ranges from 0.1:1 to 0.5:1.

Optionally, the feeding gas containing carbon monoxide comprises from 15% to 100% carbon monoxide by volume.

Optionally, the feeding gas containing carbon monoxide further comprises from 0% to 85% inactive gas by volume.

Optionally, the inactive gas is at least one of hydrogen, nitrogen, inert gas, carbon dioxide, methane and ethane.

Optionally, the inactive gas is at least one of hydrogen, nitrogen, helium, argon, carbon dioxide, methane and ethane.

Optionally, the feeding gas containing carbon monoxide further comprises at least one of hydrogen, nitrogen, helium, argon, carbon dioxide, methane and ethane.

As an embodiment, the feeding gas containing carbon monoxide may further comprise any one or more of hydrogen, nitrogen, helium, argon, carbon dioxide, methane and ethane; preferably, based on the total volume content of the feeding gas containing carbon monoxide, the volume content of carbon monoxide ranges from 15% to 100%, and the volume content of other gases such as one or more of hydrogen, nitrogen, helium, argon, carbon dioxide, methane and ethane ranges from 0 to 85%.

Optionally, the solid acid catalyst is at least one of catalysts for carbonylation of dimethyl ether.

Optionally, the solid acid catalyst is a catalyst for carbonylation of dimethyl ether.

Optionally, the solid acid catalyst is at least one of a hydrogen type zeolite molecular sieve, and a modified hydrogen type zeolite molecular sieve.

Optionally, the solid acid catalyst comprises at least one of a zeolite molecular sieve and a modified zeolite molecular sieve; wherein, the framework type of the zeolite molecular sieve is one of FER, MFI, MOR, ETL, MFS, MTF and EMT; the modification refers to at least one of element modification in which the element refers to the one other than elements constituting the framework of zeolite molecular sieve, pyridine modification, organic amine modification, alkyl ammonium halide salt modification, acid treatment, steam treatment, and ammonium ion exchange.

Optionally, the modification refers to at least one of element modification in which the element refers to the one other than elements constituting the framework of zeolite molecular sieve, pyridine modification, organic amine modification, and the modification combination (i.e., alkyl halide ammonium salt modification+acid treatment+steam treatment+ammonium ion exchange).

Optionally, the element involved in the element modification is at least one of metal elements.

Optionally, the element involved in the element modification is at least one of the metal element in group VIII, a metal element in group IB, and a metal element in group IIIA.

Optionally, the element involved in the element modification is at least one of Fe, Cu, Ag and Ga.

Optionally, the element modification, the pyridine modification, the organic amine modification, the acid treatment, the steam treatment, and the ammonium ion exchange can be achieved by methods in the prior art.

As an embodiment, the solid acid catalyst comprises one or more of the following molecular sieves: FER zeolite molecular sieve, MFI zeolite molecular sieve, MOR zeolite molecular sieve, ETL zeolite molecular sieve, MFS zeolite molecular sieve, MTF zeolite molecular sieve, EMT zeolite molecular sieve, and their modified products by the element modification in which the element refers to the one other than elements constituting the framework of zeolite molecular sieve, pyridine modification, organic amine modification, or alkyl ammonium chloride salt modification.

Optionally, the solid acid catalyst is hydrogen type zeolite molecular sieve.

Optionally, the content of the hydrogen type zeolite molecular sieve in the solid acid catalyst ranges from 10 wt % to 100 wt %.

Optionally, the content of the hydrogen type zeolite molecular sieve in the solid acid catalyst ranges from 10 wt % to 95 wt %.

Optionally, the silicon to aluminum atomic ratio of the hydrogen type zeolite molecular sieve ranges from 4 to 100.

Optionally, the zeolite molecular sieve further comprises a matrix, wherein, the matrix comprises at least one of binders.

Optionally, the solid acid catalyst comprises a matrix, and the matrix is at least one of aluminum oxide, silicon oxide, kaolin and magnesium oxide.

Optionally, the content of the hydrogen type zeolite molecular sieve in the solid acid catalyst ranges from 10 wt % to 95 wt %.

Optionally, the upper limit of the content of hydrogen zeolite molecular sieve in the solid acid catalyst is 50%, 60%, 70%, 80%, 90% or 100%; and the lower limit thereof is 50%, 60%, 70%, 80% or 90%.

As an embodiment, the solid acid catalyst is the hydrogen type product of the zeolite molecular sieve, or is composed of from 10 wt % to 95 wt % of the hydrogen type product and the balance of the matrix, or is the hydrogen type molecular sieve's modified product by the element modification in which the element refers to the one other than elements constituting the framework of zeolite molecular sieve, the pyridine modification, the organic amine modification, or the alkyl ammonium chloride salt modification, wherein the matrix is one or more of aluminum oxide, silicon oxide, kaolin and magnesium oxide.

Optionally, the alkyl ammonium halide salt is at least one of compounds having a chemical formula shown in Formula I:

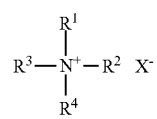

Formula I wherein $R^1$, $R^2$ and $R^3$ are independently selected from $C_1$~$C_{10}$ alkyl group;

$R^4$ is selected from one of $C_1$ to $C_{10}$ alkyl group and $C_6$ to $C_{10}$ aryl group; and X is selected from at least one of F, Cl, Br, and I.

Optionally, $R^1$, $R^2$, and $R^3$ in Formula I are independently selected from $CH_3$—, $CH_3CH_2$—, $CH_3(CH_2)_nCH_2$—, $(CH_3)_2CH$—, $(CH_3)_2CHCH_2$—, and $CH_3CH_2(CH_3)CH$—, $R^4$ is $CH_3$—, $CH_3$—, $CH_3CH_2$—, $CH_3(CH_2)_mCH_2$—, $(CH_3)_2CH$—, $(CH_3)_2CHCH_2$—, $CH_3CH_2$ $(CH_3)$ $CH$—, $C_6H_5$—, $CH_3C_6H_4$—, $(CH_3)_2C_6H_3$— or $C_6H_5CH_2$—;

wherein, n and m are independently selected from 1, 2, 3 or 4.

Optionally, X is F, Cl, Br, or I.

Optionally, the alkyl ammonium halide salt is alkyl ammonium chloride salt.

Optionally, the alkyl ammonium halide salt exchange is carried out as follow: a zeolite molecular sieve is placed in an organic ammonium salt solution at a temperature ranging 20 to 100° C. for a time ranging from 1 to 10 hours.

Optionally, the upper limit of temperature of the alkyl ammonium halide exchange is 30° C., 40° C., 50° C., 60° C., 70° C., 80° C., 90° C. or 100° C., and the lower limit of temperature thereof is 20° C., 30° C., 40° C., 50° C., 60° C., 70° C., 80° C. or 90° C.

Optionally, the upper limit of time of the alkyl ammonium halide exchange is 2 hours, 3 hours, 4 hours, 5 hours, 6 hours, 7 hours, 8 hours, 9 hours or 10 hours.

Optionally, the concentration of the alkyl ammonium halide salt aqueous solution ranges from 0.05 to 1 mol/L.

Optionally, the molecular sieve to the alkyl ammonium halide salt aqueous solution by volume ranges from 1:1 to 1:15 (g/mL).

Optionally, the solid-liquid ratio in the organic ammonium salt exchange ranges from 1 g:2 mL to 1 g:15 mL.

Optionally, the upper limit of the concentration of the alkyl ammonium halide salt solution is 0.08 mol/L, 0.1 mol/L, 0.3 mol/L, 0.5 mol/L, 0.8 mol/L or 1 mol/L; and the lower limit thereof is 0.05 mol/L, 0.08 mol/L, 0.1 mol/L, 0.3 mol/L, 0.5 mol/L or 0.8 mol/L.

Optionally, the number of times the alkyl ammonium halide salt exchange ranges from 2 to 8; and the conditions for the alkyl ammonium halide salt exchange refers to a temperature ranging from 30 to 80° C., and a time ranging from 2 to 6 hours.

Optionally, the alkyl ammonium halide salt exchange comprises: subjecting a solid containing molecular sieve to an exchange treatment in alkyl ammonium chloride salt solution at a temperature ranging from 20 to 100° C. for a time ranging from 1 to 10 hours, then washing, filtering, and drying the product; repeating the above step 2 to 8 times.

Those skilled in the art can select a suitable reactor according to actual production needs. Preferably, the reactor is a fixed bed reactor.

Optionally, the reactor is one of a fixed bed reactor, a moving bed reactor and a fluidized bed reactor.

Optionally, the reaction is a contact reaction with a catalyst.

Optionally, the reaction conditions refer to the followings: the reaction temperature ranges from 150 to 300° C., the reaction pressure ranges from 0.5 to 25.0 MPa, and the weight hourly space velocity of dimethyl ether ranges from 0.05 to 6 $h^{-1}$.

Those skilled in the art can select procedure conditions according to actual needs, such as a ratio of dimethyl ether to carbon monoxide in the raw materials, reaction temperature, reaction pressure, and space velocity.

Optionally, the upper limit of the reaction temperature is 160° C., 170° C., 200° C., 210° C., 230° C., 240° C., 260° C., 280° C., or 300° C.; and the lower limit thereof is 150° C., 160° C., 170° C., 200° C., 210° C., 230° C., 240° C., 260° C. or 280° C.

Optionally, the reaction temperature ranges from 160° C. to 280° C.

Optionally, the reaction temperature ranges from 170° C. to 260° C.

Optionally, the upper limit of the reaction pressure is 1 MPa, 6 MPa, 10 MPa, 15 MPa, 20 MPa or 25 MPa; and the lower limit thereof is 0.5 MPa, 1 MPa, 6 MPa, 10 MPa, 15 MPa or 20 MPa.

Optionally, the reaction pressure ranges from 0.5 to 20.0 MPa.

Optionally, the reaction pressure ranges from 1.0 to 15.0 MPa.

Optionally, the weight hourly space velocity of the dimethyl ether is 0.1 $h^{-1}$, 0.2 $h^{-1}$, 0.3 $h^{-1}$, 0.35 $h^{-1}$, 0.5 $h^{-1}$, 1 $h^{-1}$, 1.50 $h^{-1}$, 2.5 $h^{-1}$, 3 $h^{-1}$, 4 $h^{-1}$, 5 $h^{-1}$ or 6 $h^1$; and the lower limit thereof is 0.05 $h^{-1}$, 0.1 $h^{-1}$, 0.2 $h^{-1}$, 0.3 $h^{-1}$, 0.35 $h^{-1}$, 0.5 $h^{-1}$, 1 $h^{-1}$, 1.50 $h^{-1}$, 2.5 $h^{-1}$, 3 $h^{-1}$, 4 $h^{-1}$ or 5 $h^{-1}$.

Optionally, the weight hourly space velocity of the dimethyl ether ranges from 0.2 to 6.0 $h^{-1}$.

Optionally, the weight hourly space velocity of the dimethyl ether ranges from 0.05 to 5.0 $h^{-1}$.

Optionally, the weight hourly space velocity of the dimethyl ether ranges from 0.1 to 4.0 $h^{-1}$.

Optionally, the weight hourly space velocity of the dimethyl ether ranges from 0.2 to 4.0 $h^{-1}$.

Optionally, the weight hourly space velocity of the dimethyl ether ranges from 0.35 to 4.0 $h^{-1}$.

Optionally, the method is carried out under the following conditions: the reaction temperature ranges from 160 to 280° C., the reaction pressure ranges from 0.5 to 20.0 MPa, the weight hourly space velocity of the feeding dimethyl ether ranges from 0.05 to 5 $h^{-1}$, and the molar ratio of carbon monoxide to dimethyl ether ranges from 0.08:1 to 0.5:1.

Optionally, the method is carried out under the following conditions: the reaction temperature ranges from 170 to 260° C., the reaction pressure ranges from 1.0 to 15.0 MPa, the weight hourly space velocity of the feeding dimethyl ether ranges from 0.1 to 4.0 $h^{-1}$, and the molar ratio of carbon monoxide to dimethyl ether ranges from 0.1:1 to 0.5:1.

As an embodiment, the method comprises: feeding dimethyl ether and a feeding gas containing carbon monoxide into a reactor loaded with a solid acid catalyst to produce methyl acetate under the condition that the reaction temperature ranges from 150 to 300° C., the reaction pressure ranges from 0.5 to 25.0 MPa, the weight hourly space velocity of dimethyl ether ranges from 0.2 to 6 $h^{-1}$, and the molar ratio of carbon monoxide in the feeding gas to dimethyl ether ranges from 0.05:1 to 0.5:1.

As an embodiment, the method comprises: feeding dimethyl ether and a feeding gas containing carbon monoxide into a reactor loaded with a catalyst for carbonylation of dimethyl ether to produce methyl acetate under the condition that the reaction temperature ranges from 150 to 280° C., the reaction pressure ranges from 0.5 to 25.0 MPa, the space velocity of dimethyl ether ranges from 0.2 to 4 $h^{-1}$, and the molar ratio of carbon monoxide to dimethyl ether ranges from 0.05:1 to 0.5:1.

Optionally, the conversion rate of carbon monoxide in the method reaches greater than 20%.

Optionally, the conversion rate of carbon monoxide in the method reaches greater than 30%.

Optionally, the conversion rate of carbon monoxide in the method reaches greater than 50%.

Optionally, the conversion rate of carbon monoxide in the method reaches greater than 80%.

Optionally, the conversion rate of carbon monoxide in the method reaches greater than 90%.

Optionally, the selectivity of methyl acetate in the method reaches greater than 90%.

Optionally, the selectivity of methyl acetate in the method reaches greater than 98%.

Optionally, the selectivity of methyl acetate in the method reaches greater than 99%.

In the present application, "$C_1$~$C_{10}$", "$C_6$ to $C_{10}$" and the like all refer to the number of carbon atoms contained in the group.

In the present application, "aryl" is a group formed by the loss of any hydrogen atom on the molecule of an aromatic compound.

In the present application, "alkyl" is a group formed by the loss of any hydrogen atom on the molecule of an alkane compound.

The beneficial effects that the present application can achieve comprise:

1) The present application provides a method for producing methyl acetate by carbonylation of dimethyl ether, which has the advantages of a low molar ratio of carbon monoxide to dimethyl ether, high conversion rate of carbon monoxide, small gas circulation amount, and low operation costs and so on.

2) The present application provides a method for producing methyl acetate by carbonylation of dimethyl ether. In the method, the feeding gas containing carbon monoxide may further comprise one or more of hydrogen, nitrogen, helium, argon, carbon dioxide, methane, and ethane. Further, the volume of the carbon monoxide content ranges from 15% to 100% which is within a wide range of adjustment, thereby making the present invention possess wide application in industry and universality.

DETAILED DESCRIPTION

The present application will be described in detail below with reference to the examples, but the present application is not limited to these examples.

Unless otherwise specified, the raw materials in the examples of the present application are all commercially available. The sources of molecular sieves are shown in Table 1.

During the experiment, part of the molecular sieves can be directly purchased commercially, and the other molecular sieves can be synthesized according to the existing relevant documents. The specific sources of the molecular sieves are shown in Table 1.

TABLE 1

Sources of different molecular sieves and Si/Al atomic ratio

| Molecular sieve | Obtaining Ways | Source | Si/Al atomic ratio |
|---|---|---|---|
| NaMOR (mordenite) | purchase | Nankai University Catalyst Co., Ltd. | 6.5 |
| NaMOR (mordenite) | purchase | Nankai University Catalyst Co., Ltd. | 15 |
| NaZSM-35 | purchase | AOKE Catalyst Plant | 79 |
| NaZSM-5 | purchase | Nankai University Catalyst Co., Ltd. | 50 |
| NaEMT[1] | synthesis | Dalian Institute of Chemical Physics | 4 |
| NaEMT[1] | synthesis | Dalian Institute of Chemical Physics | 25 |
| Na-EU-12[2] | synthesis | Dalian Institute of Chemical Physics | 10 |
| Na-MCM-65[3] | synthesis | Dalian Institute of Chemical Physics | 50 |
| Na-MCM-35[3] | synthesis | Dalian Institute of Chemical Physics | 100 |
| Na-M-MOR* | synthesis | Dalian Institute of Chemical Physics | 16.5 |

The superscripts 1, 2, 3 in Table 1 are used to indicate different types of molecular sieves.

The synthesis of NaEMT with a silicon to aluminum ratio of 4 refers to Science, 2012 356(6): 70-73.

The synthesis and preparation of NaEMT with a silicon to aluminum ratio of 25 refers to the above-mentioned document and "Molecular Sieve Preparation, Secondary Synthesis and Modification": 2004:416-466 in "Molecular Sieve and Porous Material Chemistry".

The synthesis of Na-EU-12, refer to Angew. Chem. Int. Ed. 2016, 55, 7369-7373.

The synthesis of Na-MCM-65 refers to J. Phys. Chem. B 2004, 108, 15216-15222.

The synthesis of Na-MCM-35 refers to Chem. Mater. 1999, 11, 2919-2927.

Na-M-MOR represents the mordenite prepared by in-situ synthesis and modified by elements other than the elements constituting framework thereof, wherein M represents the modified metal atom. During the preparation, the metal modified molecular sieves with Fe, Ga, Cu, and Ag are prepared respectively. The content of modification metal is 0.9 wt %, and its preparation method refers to Catal. Sci. Technol., 2015 015, 5, 1961-1968.

The analysis methods in the examples of the present application are as follows.

The product gas after reaction is introduced into the online chromatograph through the heated pipeline for online analysis. The chromatograph is an Agilent 7890A equipped with a PLOT Q capillary column and a TDX-1 packed column, wherein the outlet of the PLOT-Q capillary column is connected to an FID detector, and the outlet of the TDX-1 packed column is connected to a TCD detector.

The conversion rate and selectivity in the examples of the present application are calculated as follows.

In the examples of the present application, the conversion rate of dimethyl ether, the conversion rate of carbon monoxide, and the selectivity of methyl acetate are calculated as below.

In the examples, the conversion rate of dimethyl ether and the selectivity of methyl acetate are both calculated based on the molar number of carbon of dimethyl ether.

Conversion rate of dimethyl ether=[(the molar number of carbon of dimethyl ether in raw materials)−(the molar number of carbon of dimethyl ether in the product)]÷(the molar number of carbon of dimethyl ether in the raw materials)×(100%)

Selectivity of methyl acetate=(2/3)×(the molar number of carbon of methyl acetate in the product)÷[(the molar number of carbon of dimethyl ether in the raw materials)−(the molar number of carbon of dimethyl ether in the product)]×(100%)

Conversion rate of carbon monoxide=[(the molar number of CO before reaction)−(the molar number of CO after reaction)]÷(the molar number of CO before reaction)×(100%)

As an embodiment, the method for producing methyl acetate by carbonylation of dimethyl ether comprises: feeding dimethyl ether and a feeding gas containing carbon monoxide into a reactor loaded with a solid acid catalyst to produce methyl acetate under the condition that the reaction temperature ranges from 150 to 300° C., the reaction pressure ranges from 0.5 to 25.0 MPa, the weight hourly space velocity of dimethyl ether ranges from 0.2 to 6 $h^{-1}$, and the molar ratio of carbon monoxide in the feeding gas to dimethyl ether ranges from 0.05:1 to 0.5:1.

As an embodiment, the feeding gas containing carbon monoxide may further comprise one or more of hydrogen, nitrogen, helium, argon, carbon dioxide, methane and ethane; preferably, based on the total volume content of the feeding gas containing carbon monoxide, the volume content of carbon monoxide ranges from 15% to 100%, and the volume content of other gases such as one or more of hydrogen, nitrogen, helium, argon, carbon dioxide, methane and ethane ranges from 0 to 85%.

As an embodiment, the reactor may be a fixed bed reactor, a moving bed reactor or a fluidized bed reactor.

As an embodiment, the solid acid catalyst is a catalyst for carbonylation of dimethyl ether.

As an embodiment, the solid acid catalyst comprises one or more of the following molecular sieves: FER zeolite molecular sieve, MFI zeolite molecular sieve, MOR zeolite molecular sieve, ETL zeolite molecular sieve, MFS zeolite molecular sieve, MTF zeolite molecular sieve, EMT zeolite molecular sieve, and their modified products by the element modification in which the element refers to the one other than elements constituting the framework of zeolite molecular sieve, pyridine modification, organic amine modification, or alkyl ammonium chloride salt modification.

As an embodiment, the solid acid catalyst is the hydrogen type product of the zeolite molecular sieve, or is composed of from 10 wt % to 95 wt % of the hydrogen type product and the balance of the matrix, or is the hydrogen type molecular sieve's modified product by the element modification in which the element refers to the one other than elements constituting the framework of zeolite molecular sieve, the pyridine modification, the organic amine modification, or the alkyl ammonium chloride salt modification, wherein the matrix is one or more of aluminum oxide, silicon oxide, kaolin and magnesium oxide.

As an embodiment, the carbonylation is carried out under the condition that a reaction temperature ranges from 160 to 280° C., a reaction pressure ranges from 0.5 to 20.0 MPa, a weight hourly space velocity of the feeing dimethyl ether ranges from 0.05 to 5 $h^{-1}$, and the molar ratio of carbon monoxide to dimethyl ether ranges from 0.08:1 to 0.5:1.

As an embodiment, the reaction temperature ranges from 170 to 260° C., the reaction pressure ranges from 1.0 to 15.0 MPa, the weight hourly space velocity of the feeding dimethyl ether ranges from 0.1 to 4.0 $h^{-1}$, and the molar ratio of carbon monoxide to dimethyl ether ranges from 0.1:1 to 0.5:1.

Example 1

Preparation of Hydrogen Type Molecular Sieve.

The Na-type molecular sieve in Table 1 is subjected to $NH_4NO_3$ ion exchange, then dried and calcined to obtain a hydrogen type molecular sieve. For example, a typical process for preparing hydrogen type molecular sieve is as follows: NaMOR molecular sieve powder is added to a pre-prepared 1 mol/L $NH_4NO_3$ aqueous solution in a hydrothermal synthesis reactor, with a solid-liquid mass ratio of 1:10. The exchange reaction is carried out at 80° C. for 2 hours under stirring, and the resulting product is then subjected to vacuum filtration and washing with water. After three consecutive exchange reactions, the resulting product is then dried at 120° C. overnight, and calcined at 550° C. for 4 h to obtain the desired HMOR catalyst sample.

The parameters for preparing hydrogen molecular sieves by the rest molecular sieves in Table 1 are the same as the above process with exception of the molecular sieve.

Formed hydrogen type samples containing matrix are prepared by extrusion molding. For example, a typical preparation process of the formed sample is as follows: 80 g Na-MOR and 20 g alumina are thoroughly mixed, 10 wt % nitric acid is then added therein for kneading, and the resulting sample kneaded into lumpy shape is extruded into formed strips by an extruder. The extruded strip samples are dried at 120° C., calcined at 550° C. for 4 h, and then is subjected to the above process for preparing the hydrogen type molecular sieve to prepare the formed hydrogen type sample containing the matrix.

The parameters for preparing the hydrogen type samples containing matrix via the rest molecular sieves in Table 1 are the same as above process with exception of the molecular sieve type and matrix type.

Preparation of pyridine-modified hydrogen type samples: A typical preparation process is as follows, 10 g hydrogen type sample is loaded into a reaction tube, gradually heated to 550° C. under a nitrogen atmosphere at a rate of 100 mL/min, maintained for 4 hours, and is subjected to treatment with pyridine carried by nitrogen at 350° C. for 4 hours to prepare pyridine-modified samples. The samples were marked with H-M'-py, where M' represents the name of the molecular sieve.

The parameters for preparing the pyridine-modified molecular sieve by the rest molecular sieves in Table 1 are the same as the above process with exception of the molecular sieve.

A series of samples prepared according to the above processes are shown in Table 2.

TABLE 2

Number and Composition of the prepared samples

| Catalyst Number | Catalyst | Si/Al ratio of molecular sieve | Content of molecular sieve | Matrix type | Matrix content |
|---|---|---|---|---|---|
| 1# | H-MOR | 6.5 | 100 wt % | — | 0% |
| 2# | H-MOR | 6.5 | 50 wt % | Silicon oxide + Aluminum oxide + Magnesium oxide (mass ratio thereof is 2:2:1) | 50 wt % |
| 3# | H-MOR | 15 | 80 wt % | Aluminum oxide | 20 wt % |
| 4# | H-ZSM-35 | 79 | 80 wt % | Kaolin | 20 wt % |
| 5# | H-ZSM-5 | 50 | 70 wt % | Aluminum oxide | 30 wt % |
| 6# | H-EMT | 4 | 80 wt % | Aluminum oxide | 20 wt % |
| 7# | H-EMT | 25 | 80 wt % | Aluminum oxide | 20 wt % |
| 8# | H-EU-12 | 10 | 80 wt % | Aluminum oxide | 20 wt % |
| 9# | H-MCM-65 | 50 | 80 wt % | Aluminum oxide | 20 wt % |
| 10# | H-MCM-35 | 100 | 90 wt % | Aluminum oxide | 10 wt % |
| 11# | H-MOR-py | 15 | 80 wt % | Aluminum oxide | 20 wt % |
| 12# | H-EMT-py | 25 | 80 wt % | Aluminum oxide | 20 wt % |
| 13# | H—Fe-MOR | 16.5 | 100 wt % | — | 0% |
| 14# | H—Cu-MOR | 16.5 | 100 wt % | — | 0% |
| 15# | H—Ag-MOR | 16.5 | 100 wt % | — | 0% |
| 16# | H—Ga-MOR | 16.5 | 100 wt % | — | 0% |

Example 2

100 g Na-MOR (Si/Al=15) molecular sieve are respectively added into 1000 mL 0.5 mol/L tetraethylmethylammonium chloride aqueous solution, phenyltrimethylammonium chloride aqueous solution, benzyltrimethylammonium chloride aqueous solution, benzyltrimethylammonium bromide aqueous solution, benzyltrimethylammonium iodide aqueous solution and then are treated at 80° C. for 4 hours. After subsequent filtering and drying steps, the above exchange process is repeated 5 times. Then, the resulting samples are respectively added into 1000 mL 0.7 mol/L oxalic acid aqueous solution, and are treated at 60° C. for 3 hours to undergo acid treatment. After subsequent filtering and drying steps, the above acid treatment process is repeated 3 times. Then, the resulting samples are respectively treated in an air atmosphere with a steam concentration of 10% at 650° C. for 4 hours. Then the samples obtained by the high temperature and steam treatment are respectively treated in 1000 mL 1 mol/L ammonium nitrate aqueous solution at 70° C. for 4 hours to undergo ammonium nitrate solution exchange treatment. After washing and drying steps, the ammonium nitrate solution exchange treatment process is repeated 3 times. Then, the samples obtained are respectively calcined at 550° C. for 4 hours under an air atmosphere to obtain 17# catalyst, 18# catalyst, 19# catalyst, 20# catalyst, and 21# catalyst respectively.

Example 3

10 g HMOR (Si/Al=6.5) sample prepared in Example 1 is gradually raised to 550° C. at a rate of 100 mL/min under a nitrogen atmosphere, and maintained for 4 hours, followed by treatment with trimethylamine carried by nitrogen and tetraethylammonium carried by nitrogen respectively at 200° C. for 4 hours, to obtain organic amine modified 22# catalyst and 23# catalyst respectively.

The catalytic performance of the above-mentioned catalysts is investigated under the following conditions.

10 g catalyst is loaded into a fixed bed reactor with inner diameter of 28 mm, in which the temperature is raised to 550° C. at a rate of 5° C./min under a nitrogen atmosphere, and is maintained 4 hours. Then the temperature is lowered to 250° C. under the nitrogen atmosphere. The pressure in the reaction system is increased to 5 MPa by using CO. The reaction raw materials are passed through the catalyst bed from top to bottom. The weight hourly space velocity of the feeding dimethyl ether is 1.50 $h^{-1}$. The molar ratio of carbon monoxide to dimethyl ether is 0.45:1, and the feeding gas containing carbon monoxide does not comprise other gases. Under the reaction temperature is 250° C. and the catalytic reaction was run 2 hours, the reaction results are shown in Table 3. The catalytic results of 11# catalyst for carbonylation of dimethyl ether under different operation time are shown in Table 4.

TABLE 3

Reaction results of different catalysts for carbonylation of dimethyl ether

| Catalyst | CO Conversion rate (%) | Conversion rate of dimethyl ether (%) | Selectivity of methyl acetate (%) | Selectivity of other product (%) |
|---|---|---|---|---|
| 1# | 71.5 | 35.8 | 99.9 | 0.1 |
| 2# | 47.3 | 23.7 | 99.8 | 0.2 |
| 3# | 62.1 | 31.1 | 99.5 | 0.5 |
| 4# | 44.5 | 22.3 | 99.3 | 0.7 |
| 5# | 27.5 | 13.8 | 99.6 | 0.4 |
| 6# | 76.9 | 38.5 | 99.5 | 0.5 |
| 7# | 65.9 | 33.0 | 99.6 | 0.4 |
| 8# | 38.3 | 19.2 | 99.5 | 0.5 |
| 9# | 24.2 | 12.1 | 92.6 | 7.4 |
| 10# | 36.8 | 18.4 | 94.5 | 5.5 |
| 11# | 98.8 | 49.5 | 99.9 | 0.1 |
| 12# | 98.5 | 49.4 | 99.2 | 1.7 |
| 13# | 57.6 | 28.9 | 98.4 | 1.6 |
| 14# | 52.1 | 26.1 | 97.5 | 2.5 |
| 15# | 55.6 | 27.9 | 98.8 | 1.2 |
| 16# | 53.8 | 27.0 | 90.8 | 9.2 |
| 17# | 96.5 | 49.9 | 98.9 | 1.1 |
| 18# | 97.5 | 49.9 | 98.9 | 1.1 |

TABLE 3-continued

Reaction results of different catalysts for carbonylation of dimethyl ether

| Catalyst | CO Conversion rate (%) | Conversion rate of dimethyl ether (%) | Selectivity of methyl acetate (%) | Selectivity of other product (%) |
|---|---|---|---|---|
| 19# | 97.5 | 49.9 | 98.9 | 1.1 |
| 20# | 97.6 | 49.9 | 98.9 | 1.1 |
| 21# | 98.1 | 50.0 | 98.7 | 1.3 |
| 22# | 52.3 | 26.0 | 98.7 | 1.3 |
| 23# | 56.8 | 28.4 | 98.7 | 1.3 |

TABLE 4

Catalytic results of 11# catalyst for carbonylation of dimethyl ether

| Running time (h) | CO Conversion rate (%) | Conversion rate of dimethyl ether (%) | Selectivity of methyl acetate (%) | Selectivity of other product (%) |
|---|---|---|---|---|
| 2 | 98.8 | 49.5 | 99.9 | 0.1 |
| 200 | 98.7 | 49.5 | 99.9 | 0.1 |
| 1000 | 98.5 | 49.4 | 99.9 | 0.1 |
| 4000 | 98.3 | 49.3 | 99.7 | 0.3 |
| 6000 | 97.9 | 49.1 | 98.6 | 1.4 |
| 8000 | 96.9 | 48.6 | 97.5 | 2.5 |

Example 4

Reaction Results of Carbonylation of Dimethyl Ether at Different Reaction Temperatures 10 g 17# catalyst is loaded into the fixed-bed reactor with an inner diameter of 28 mm. The temperature is raised to 550° C. at a rate of 5° C./min under a nitrogen atmosphere, and is maintained for 4 hours. Then, the temperature is lowered to the reaction temperature under the nitrogen atmosphere. The pressure in the reaction system is increased to 5 MPa by using CO. The reaction raw materials are passed through the catalyst bed from top to bottom. The weight hourly space velocity of the feeding dimethyl ether is 1.50 $h^{-1}$. The molar ratio of carbon monoxide to dimethyl ether is 0.45:1, and the feeding gas containing carbon monoxide does not comprise other gases. The reaction temperature are 150° C., 160° C., 170° C., 200° C., 230° C., 240° C., 260° C., 280° C. and 300° C. respectively. The reaction results of the catalytic reaction running for 100 hours were shown in Table 5.

TABLE 5

Reaction results at different reaction temperatures

| | | | | | | | | | |
|---|---|---|---|---|---|---|---|---|---|
| The temperature at the inlet of the reactor | 150 | 160 | 170 | 200 | 230 | 240 | 260 | 280 | 300 |
| Conversion rate of dimethyl ether (%) | 1.0 | 3.5 | 7.9 | 21.2 | 38.2 | 42.6 | 45.2 | 47.8 | 49.9 |
| CO Conversion rate (%) | 2.0 | 7.0 | 15.7 | 42.1 | 76.0 | 85.2 | 90.4 | 95.6 | 99.9 |
| Selectivity of methyl acetate (%) | 97.5 | 97.7 | 97.8 | 99.7 | 99.5 | 99.1 | 99.3 | 99.5 | 99.1 |
| Selectivity of other product (%) | 2.5 | 2.3 | 2.2 | 0.3 | 0.5 | 0.9 | 0.7 | 0.5 | 0.9 |

Example 5

Reaction results of the carbonylation of dimethyl ether under different reaction pressures are shown as below.

10 g 17# catalyst is loaded into the fixed-bed reactor with an inner diameter of 28 mm. The temperature is raised to 550° C. at a rate of 5° C./min under a nitrogen atmosphere, and is maintained for 4 hours. Then, the temperature is lowered to 220° C. under the nitrogen atmosphere. The pressure in the reaction system is increased to 5 MPa by using CO. The reaction raw materials are passed through the catalyst bed from top to bottom. The weight hourly space velocity of the feeding dimethyl ether is 1.50 $h^{-1}$. The molar ratio of carbon monoxide to dimethyl ether is 0.45:1, and the feeding gas containing carbon monoxide does not comprise other gases. The reaction pressures are 0.5 MPa, 1 MPa, 6 MPa, 10 MPa, 15 MPa, 20 MPa and 25 MPa respectively. The reaction results of the catalytic reaction running for 100 hours are shown in Table 6.

TABLE 6

Reaction results under different reaction pressures

| | | | | | | | |
|---|---|---|---|---|---|---|---|
| Reaction Pressure (MPa) | 0.5 | 1 | 6 | 10 | 15 | 20 | 25 |
| Conversion rate of dimethyl ether (%) | 5.2 | 9.2 | 29.8 | 36.6 | 41.5 | 43.5 | 45.8 |
| CO Conversion rate (%) | 10.4 | 18.3 | 59.3 | 72.8 | 82.3 | 87.0 | 92.0 |
| Selectivity of methyl acetate (%) | 97.8 | 98.7 | 99.9 | 99.9 | 99.9 | 99.9 | 99.9 |
| Selectivity of other product (%) | 2.2 | 1.3 | 0.1 | 0.1 | 0.1 | 0.1 | 0.1 |

Example 6

Reaction results of the carbonylation of dimethyl ether at different space velocities of dimethyl ether are as below.

10 g 17# catalyst is loaded into the fixed-bed reactor with an inner diameter of 28 mm. The temperature is raised to 550° C. at a rate of 5° C./min under a nitrogen atmosphere, and is maintained for 4 hours. Then, the temperature is lowered to 235° C. under the nitrogen atmosphere. The pressure in the reaction system was increased to 8 MPa by using CO. The reaction raw materials are passed through the catalyst bed from top to bottom. The molar ratio of carbon monoxide to dimethyl ether is 0.45:1, the feeding gas containing carbon monoxide does not comprise other gases, and the weight hourly space velocity of the feeding dimethyl ether are 0.05 $h^{-1}$, 0.1 $h^{-1}$, 0.2 $h^{-1}$, 0.35 $h^{-1}$, 1 $h^{-1}$, 2.5 $h^{-1}$, 4 $h^{-1}$ and 6 $h^{-1}$ respectively. When the reaction was run for 100 hours, the reaction results are shown in Table 7.

TABLE 7

Reaction results under different weight hourly space velocities of dimethyl ether

| | | | | | | | | |
|---|---|---|---|---|---|---|---|---|
| Weight hourly space velocity of the feeding dimethyl ether ($h^{-1}$) | 0.05 | 0.1 | 0.2 | 0.35 | 1 | 2.5 | 4 | 6 |
| Conversion rate of dimethyl ether (%) | 50.0 | 50.0 | 50.0 | 50.0 | 47.9 | 27.8 | 12.5 | 6.3 |
| CO Conversion rate (%) | 100 | 100 | 100 | 100 | 95.4 | 55.26 | 24.8 | 13.6 |
| Selectivity of methyl acetate (%) | 97.6 | 98.6 | 99.2 | 99.9 | 99.8 | 99.2 | 98.7 | 98.5 |
| Selectivity of other product (%) | 2.4 | 1.4 | 0.8 | 0.1 | 0.2 | 0.8 | 1.3 | 1.5 |

Example 7

Reaction results of carbonylation of dimethyl ether under different molar ratios of carbon monoxide to dimethyl ether are as below.

10 g 17# catalyst is loaded into the fixed-bed reactor with an inner diameter of 28 mm. The temperature is raised to 550° C. at a rate of 5° C./min under a nitrogen atmosphere, and is maintained for 4 hours. Then, the temperature is lowered to 235° C. under the nitrogen atmosphere. The pressure in the reaction system is increased to 8 MPa by using CO. The reaction raw materials are passed through the catalyst bed from top to bottom. The weight hourly space velocity of the feeding dimethyl ether is 1.0 $h^{-1}$. The feeding gas containing carbon monoxide does not comprise other gases. The molar ratios of carbon monoxide to dimethyl ether are 0.05:1, 0.08:1, 0.1:1, 0.2:1, 0.45:1, 0.48:1, 0.498:1, 0.5:1 respectively. When the reaction is run for 100 hours, the reaction results are shown in Table 8.

TABLE 8

Reaction results under different molar ratios of carbon monoxide to dimethyl ether

| | | | | | | | | |
|---|---|---|---|---|---|---|---|---|
| Molar ratio of carbon monoxide to dimethyl ether | 0.05:1 | 0.08:1 | 0.1:1 | 0.2:1 | 0.45:1 | 0.48:1 | 0.498:1 | 0.5:1 |
| Conversion rate of carbon monoxide (%) | 89.7 | 90.2 | 90.6 | 92.9 | 93.8 | 94.6 | 97.8 | 98.1 |

TABLE 8-continued

Reaction results under different molar ratios of carbon monoxide to dimethyl ether

| Conversion rate of dimethyl ether (%) | 4.5 | 7.2 | 9.06 | 18.6 | 42.1 | 45.5 | 48.7 | 49.0 |
|---|---|---|---|---|---|---|---|---|
| Selectivity of methyl acetate (%) | 99.3 | 99.3 | 99.3 | 99.4 | 99.4 | 99.3 | 99.4 | 99.3 |

Example 8

Reaction results of carbonylation of dimethyl ether under the feeding gas containing carbon monoxide comprises inert gas are as below.

10 g 13# catalyst is loaded into the fixed-bed reactor with an inner diameter of 28 mm. The temperature is raised to 550° C. at a rate of 5° C./min under a nitrogen atmosphere, and is maintained for 4 hours. Then, the temperature is lowered to 235° C. under the nitrogen atmosphere. The pressure in the reaction system is increased to 10 MPa by using CO. The reaction raw materials are passed through the catalyst bed from top to bottom. The weight hourly space velocity of the feeding dimethyl ether feed is 1.0 $h^{-1}$. The feeding gas containing carbon monoxide comprises inert gas. The molar ratio of DME/CO is shown in Table 9. According to the ratio of DME/CO, the amount of the feeding gas containing carbon monoxide is adjusted. When the reaction is run for 100 hours, the reaction results with different inert gases are shown in Table 9.

TABLE 9

Reaction results under the feeding gas containing carbon monoxide comprises inert gas

| Feeding gas containing carbon monoxide | | | Conversion rate of dimethyl ether (%) | Conversion rate of carbon monoxide (%) | Selectivity of methyl acetate (%) |
|---|---|---|---|---|---|
| Volume content of inert gas (%) | Volume content of CO (%) | CO/DME ratio | | | |
| 85 ($N_2$) | 15 | 0.3 | 17.6 | 58.6 | 99.8 |
| 70 ($N_2$) | 30 | 0.3 | 25.8 | 86.0 | 99.8 |
| 28 ($N_2$) + 5 ($CO_2$) + 10 (Ar) + 7 ($H_2$) | 50 | 0.3 | 29.5 | 98.3 | 99.5 |

Example 9

10 g 17# catalyst was loaded into a fluidized bed reactor and a moving bed reactor respectively. The temperature is raised to 550° C. at a rate of 5° C./min under a nitrogen atmosphere, and is maintained for 4 hours. Then, the temperature is lowered to 240° C. under the nitrogen atmosphere. The pressure in the reaction system is increased to 8 MPa by using CO. The space velocity of the feeding dimethyl ether is 1.50 $h^{-1}$. The molar ratio of carbon monoxide to dimethyl ether is 0.45:1, and the feeding gas containing carbon monoxide does not comprise other gases. When the catalytic reaction is run 100 hours, the reaction results are shown in Table 10.

TABLE 10

Reaction results at different reactor types

| Reactor type | Conversion rate of dimethyl ether (%) | Conversion rate of carbon monoxide (%) | Selectivity of methyl acetate (%) |
|---|---|---|---|
| Fluidized bed reactor | 48.0 | 95.9 | 99.8 |
| Moving bed reactor | 46.9 | 93.8 | 99.8 |

The above examples are only illustrative, and do not limit the present application in any form. Any change or modification, made by the skilled in the art based on the technical content disclosed above, without departing from the spirit of the present application, is equivalent example and falls within the scope of the present application.

The invention claimed is:

1. A method for producing methyl acetate by carbonylation of dimethyl ether comprising, feeding dimethyl ether and a feeding gas containing carbon monoxide into a reactor equipped with a solid acid catalyst to react to produce methyl acetate;
   wherein, a molar ratio of carbon monoxide to dimethyl ether ranges from 0.05:1 to 0.5:1;
   wherein the solid acid catalyst comprises at least one of a zeolite molecular sieve and a modified zeolite molecular sieve;
   wherein, a framework type of the zeolite molecular sieve is one of FER, MFI, MOR, ETL, MFS, MTF, and EMT; and a modification refers to at least one of element modification in which the element refers to the one other than elements constituting a framework of zeolite molecular sieve, pyridine modification, organic amine modification, alkyl ammonium halide salt modification, acid treatment, steam treatment, and ammonium ion exchange;
   wherein the zeolite molecular sieve is hydrogen type zeolite molecular sieve;
   wherein a content of the hydrogen type zeolite molecular sieve in the solid acid catalyst ranges from 10 wt % to 100 wt %.

2. The method according to claim 1, wherein the molar ratio of carbon monoxide to dimethyl ether ranges from 0.08:1 to 0.5:1.

3. The method according to claim 2, wherein the molar ratio of carbon monoxide to dimethyl ether ranges from 0.1:1 to 0.5:1.

4. The method according to claim 1, wherein the feeding gas containing carbon monoxide comprises from 15% to 100% carbon monoxide by volume.

5. The method according to claim 1, wherein the feeding gas containing carbon monoxide further comprises at least one of hydrogen, nitrogen, helium, argon, carbon dioxide, methane and ethane.

6. The method according to claim 1, wherein a content of the hydrogen type zeolite molecular sieve in the solid acid catalyst ranges from 10 wt % to 95 wt %.

7. The method according to claim 1, wherein the solid acid catalyst comprises a matrix; and the matrix is at least one of aluminum oxide, silicon oxide, kaolin and magnesium oxide.

8. The method according to claim 1, wherein the reactor is one of a fixed bed reactor, a moving bed reactor, and a fluidized bed reactor.

9. The method according to claim 1, wherein reaction conditions refer to the followings: a reaction temperature ranges from 150° C. to 300° C., a reaction pressure ranges from 0.5 to 25.0 MPa, and a weight hourly space velocity of dimethyl ether ranges from 0.05 $h^{-1}$ to 6 $h^{-1}$.

10. The method according to claim 9, wherein the reaction temperature ranges from 160° C. to 280° C.

11. The method according to claim 10, wherein the reaction temperature ranges from 170° C. to 260° C.

12. The method according to claim 9, wherein the reaction pressure ranges from 0.5 MPa to 20.0 MPa.

13. The method according to claim 12, wherein the reaction pressure ranges from 1.0 MPa to 5.0 MPa.

14. The method according to claim 9, wherein the weight hourly space velocity of dimethyl ether ranges from 0.2 $h^{-1}$ to 6.0 $h^{-1}$.

15. The method according to claim 9, wherein the weight hourly space velocity of dimethyl ether ranges from 0.1 $h^{-1}$ to 4.0 $h^{-1}$.

16. The method according to claim 15, wherein the weight hourly space velocity of dimethyl ether ranges from 0.35 $h^{-1}$ to 4.0 $h^{-1}$.

* * * * *